United States Patent [19]

Ackermann et al.

[11] 4,043,873

[45] Aug. 23, 1977

[54] PLURAL STAGE RECOVERY OF TRIOXANE IN A PROCESS HAVING A MOLECULAR DISTILLATION STEP

[75] Inventors: Jacob Ackermann, Wigoltingen, Switzerland; Pierino Radici, Turate (Como); Umberto Santini, Legnano (Milan); Paolo Colombo, Saronno (Varese), all of Italy

[73] Assignee: Societa' Italiana Resine S.I.R. S.p.A., Milan, Italy

[21] Appl. No.: 677,952

[22] Filed: Apr. 19, 1976

Related U.S. Application Data

[63] Continuation of Ser. No. 480,449, June 17, 1974, abandoned.

[30] Foreign Application Priority Data

June 15, 1973 Italy .................................. 25410/73

[51] Int. Cl.² .......................................... B01D 3/12
[52] U.S. Cl. ...................................... 203/46; 203/77; 203/7; 203/72; 203/80; 203/89; 203/91; 260/340

[58] Field of Search .................... 260/340; 203/46, 72, 203/89, 91, 88, 7, 43, 71, 77, 80

[56] References Cited

U.S. PATENT DOCUMENTS 3,395,157 7/1968 Dankert et al. ...................... 260/340

Primary Examiner—Frank W. Lutter
Assistant Examiner—Frank Sever
Attorney, Agent, or Firm—Sughrue, Rothwell, Mion, Zinn and Macpeak

[57] ABSTRACT

Process for the separation of trioxane from aqueous solutions containing it together with formaldehyde, which comprises subjecting the said solutions to evaporation at temperatures of 100° C or lower, at pressures lower than atmospheric, and with residence times of less than 1 minute under the evaporation conditions, with vaporization of a quantity of from about 5 to about 15% by weight of the solution introduced, and recovering the trioxane from the products evaporated in this way.

15 Claims, 1 Drawing Figure

PLURAL STAGE RECOVERY OF TRIOXANE IN A PROCESS HAVING A MOLECULAR DISTILLATION STEP

This is a Continuation of application Ser. No. 480,449, filed June 17, 1974, now abandoned.

BACKGROUND OF THE INVENTION

1. Field of the Invention

The present invention relates to the production of the cyclic trimmer of formaldehyde, and it relates in particular to the separation of said trimer from the aqueous solutions containing it together with formaldehyde.

2. Description of the Prior Art

The cyclic trimer of formaldehyde is commonly known as trioxane, and this name will be used in the following description. As is known, trioxane is formed in concentrated aqueous solutions of formaldehyde when acidic substances are added to such solutions (Journal of the Chemical Society - London 121, 1922). In this way an equilibrium is established between the formaldehyde and its timer, the said equilibrium depending on the initial concentration of formaldehyde in the solution. The concentrated aqueous solutions of formaldehyde that are suitable for the production of trioxane can be obtained by evaporation of less concentrated solutions, for example commercial formalins, or by dissolutions of low polymers of formaldehyde, such as paraformaldehyde, in water.

The methods used for the separation of the trioxane from the reaction medium are generally based on the distillation of an azeotrope with water. In the absence of formaldehyde this azeotrope consists of 70% by weight of trioxane and 30% by weight of water, with a boiling point of 91.3° C at atmospheric pressure. The trioxane is recovered from the distillate by extraction with a solvent that is immiscible with water, followed by fractional distillation of the organic phase obtained in this way.

A disadvantage of this process is that more or less large quantities of formaldehyde, depending on the composition of the starting mixture, distil during the distillation of the trioxane-water azeotrope (see U.S. Pat. No. 2,347,447), and the composition of the distillate also varies according to the distillation rate.

Thus industrially acceptable distillation rates are obtained if temperatures of from 93° to about 97° C are maintained at the top of the column. Under these conditions the quantity of trioxane in the distillate lies within a range of values from about 20 to about 40% by weight, while the quantity of formaldehyde varies from about 10 to about 40% by weight. When temperatures of about 91° to about 93° C are maintained at the top of the distillation column, a distillate that is richer in trioxane is obtained, but the distillation rate decreases so that it becomes industrially unacceptable.

A decrease in the content of formaldehyde and an increase in the content of trioxane at the top of the distillation column are therefore obtained if high reflux ratios are maintained, the said ratios generally being greater than 3.

However, this procedure has various disadvantages, such as the deterioration of the energy balance in relation to the trioxane produced and the long residence time at the distillation temperatures, with the result that the formation of by-products derived from formaldehyde through secondary reactions, such as the Cannizzaro reaction (formation of methanol and formic acid) and the Tishchenko reaction (formation of methyl formate), is favored.

A further disadvantage of the said distillation procedure is that the formaldehyde that rises to the top of the column is readily deposited in the form of a polymer on the cooler parts of the apparatus. This phenomenon, which is observed especially in processes in which high distillation rates are used, causes incrustation and blockage of pipes and similar parts. It therefore follows that the operation of the column has to be interrupted to remove the deposited polymer, e.g., by treatment with steam. The deposition of the polymer is related not only to the total concentration of formaldehyde but also to the concentration of trioxane in the fraction that separates at the top of the distillation column. In addition to the undesirable interruptions, therefore, the processes of prior art have the further disadvantage inherent in the loss of rather considerable quantities of formaldehyde.

This last disadvantage can be partly avoided, according to a known technique (see Italian Pat. No. 671,941) by introduction of lower aliphatic alcohols such as methanol and ethanol, or of their hemiformals, into the boiling system. Owing to the range of conditions used, however, reaction by-products such as methylals, which, when methanol is used, have the following general formula:

$$CH_3-O(CH_2O)_n CH_3$$

where $n$ generally has values of from 1 to 3, are formed. This fact, besides leading to losses of formaldehyde, does not allow the production of trioxane with a high purity. This is because the separation of the methylals is very difficult owing to a certain chemical affinity for trioxane and also owing to the closeness of certain physical constants such as the boiling point and those connected with the extractability with solvent.

On the other hand, the trioxane is mainly used for the production of acetal homopolymers and copolymers, for which a monomer of very high purity is required both in the case of cationic polymerization and in the case of free-radical polymerization.

Another limiting factor in the known processes is the fact that the distillation rate is determined by the kinetics of formation of trioxane in the reaction mixture contained in the boiler of the column, the said boiler also acting as the trimerization reactor, in which, for the system in question, it is convenient to work with trioxane concentrations very close to the equilibrium concentration. It is therefore necessary to maintain sufficiently long residence times so that as the distillation proceeds, a trioxane concentration such as to ensure a constant feed to the distillation column is formed in the reaction mixture.

SUMMARY

Figure 1:
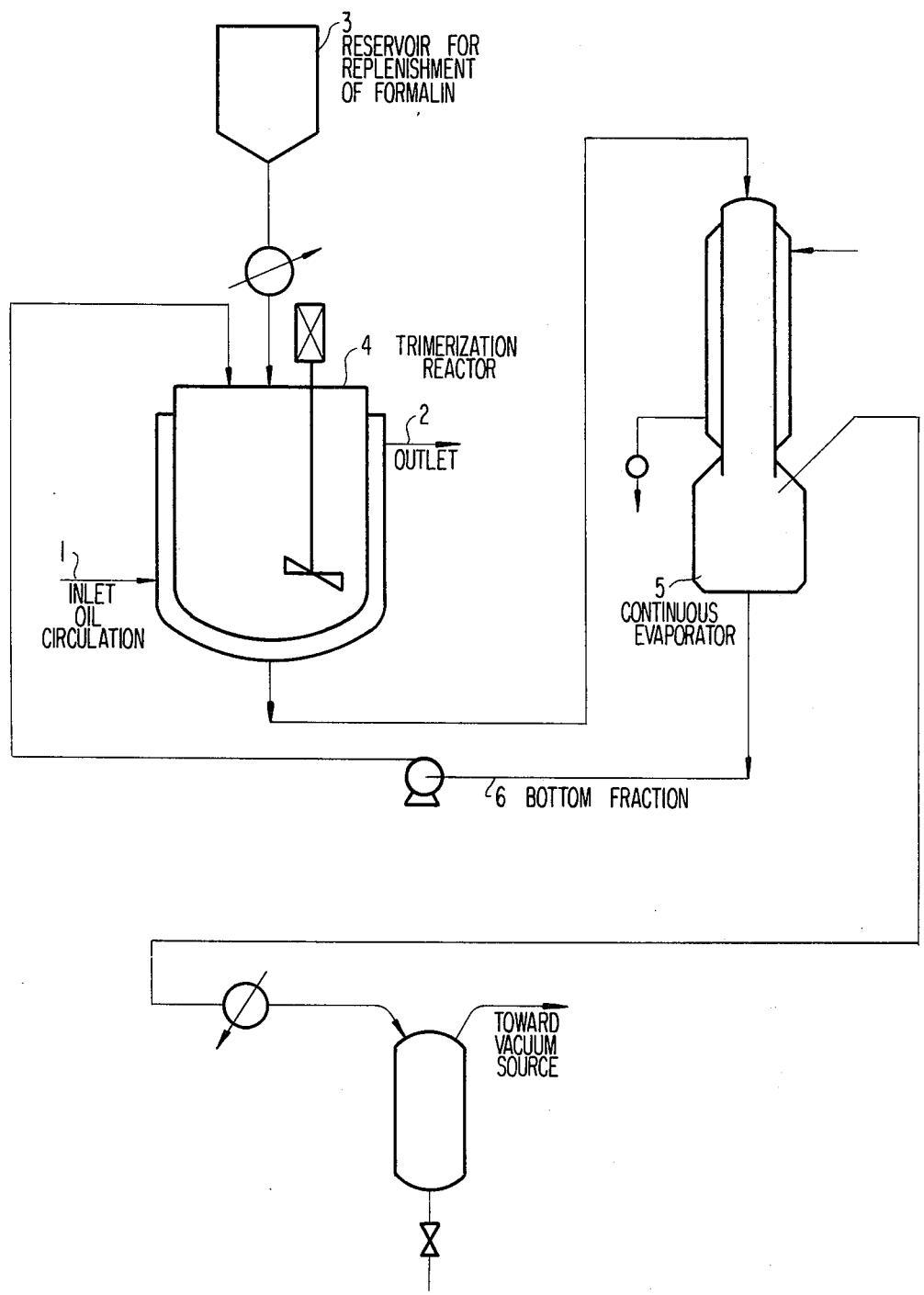
In FIG. 1, which represents an embodiment of this invention, 1 and 2 represent the inlet and outlet respectively, of the oil circulation. The reservoir of the replenishment of formalin is represented by 3 while 4 is the trimerization reactor and 5 is the continuous evaporator. The bottom fraction stream is shown as 6.

It is an object of the invention to provide a process for the separation of trioxane from aqueous solutions containing it together with formaldehyde and the trimerization catalyst, which allows the disadvantages of the processes of prior art to be avoided or at least considerably reduced. Other objects and advantages of this invention will be apparent from the description and claims following.

The process of the present invention is based essentially on the rapid or "instantaneous" vaporization of limited quantities of the aqueous solution containing trioxane and formaldehyde.

More precisely, the said aqueous solution is subjected to evaporation at temperatures of about 100° C or lower, at pressures below atmospheric and with residence times under the evaporation conditions of less than one minute, with vaporization of a quantity of from about 5 to about 15% by weight of the solution.

It is found that working under the conditions specified by the present invention favours the enrichment of trioxane in the vapour phase in relation to the other components present in the reaction mixture. The concentration of trioxane in the distillate therefore has a value in the range from about 10 to about 35% by weight, depending on the composition of the solution that is subjected to vaporization, while the corresponding concentrations of formaldehyde vary from about 8 to about 35% by weight.

In other words, by operation in accordance with the present invention, the trioxane/formaldehyde ratio in the distillate is improved to such an extent that the danger of deposition of polymers of formaldehyde on the cooler parts of the apparatus is eliminated. The formaldehyde losses inherent in the processes of prior art are consequently avoided.

Moreover, owing to the short residence times under the distillation conditions, the possibility of secondary reactions leading to the formation of by-products is reduced to a minimum. It is thus possible to obtain trioxane of high purity.

Finally, by operation in accordance with the present invention, considerable economic advantages are achieved, since the energy necessary to obtain a given quantity of trioxane is comparatively rather lower than that required in the processes of the prior art.

The trimerization reaction of formaldehyde is carried out, according to the known technique, in aqueous solutions having a formaldehyde content of from 30 to 85% by weight and preferably from 40 to 80% by weight, at temperatures of from 20° to 150° C, preferably from 80° to 110° C, in the presence of acid catalysts. Strong or medium-strong mineral acids that do not react with formaldehyde or with the other compounds present in the reaction medium are generally used for this purpose.

The preferred catalysts are sulphuric, perchloric, and phosphoric acids. Sulphuric acid is especially preferred. Strong or medium-strong organic acids, such as aromatic sulphonic acids, e.g. toluenesulphonic acids, can also be used for the purpose. Finally, strong or medium-strong acid ion exchangers, particularly those containing free sulphonic groups, can also be used as trimerization catalysts. The concentration of the catalyst in the reaction medium can vary within a wide range of values; in the case of sulphuric acid the limits range from about 0.5 to about 7.0% by weight.

Under the conditions described, an equilibrium is established between formaldehyde and trioxane in the aqueous reaction medium, the said equilibrium depending on the initial formaldehyde concentration.

As was mentioned earlier, the reaction mixture obtained in this way is subjected to vaporization. More particularly, the vaporization of limited quantities of the solution, and more precisely of a quantity of from about 5 to about 15% by weight, is carried out in "instantaneous" distillation apparatus, for example by the thin-film or the molecular distillation technique. The evaporation is carried out at pressures below atmospheric, normally at values in the range from about 20 to about 700 mmHg, and preferably from about 50 to about 500 mmHg, with residence times of less than about 1 minute, and generally of about 3 to about 45 seconds, under the distillation conditions.

For this purpose the products of the trimerization reaction are fed continuously into the apparatus intended for the vaporization, with a feed rate that depends on the trimerization kinetics.

It is known, on the other hand, that for each concentration of the aqueous formaldehyde solutions there is, for each temperature, a limiting time beyond which precipitation of solid polyoxymethylenes is observed, and for each concentration of the said solution there is a limiting value for the temperture (stability temperature) above which the precipitation phenomenon no longer occurs.

According to one embodiment of the process of the present invention, the evaporation is carried out in a range of temperatures below the stability temperatures of the aqueous formaldehyde solutions, and generally between 20 and 35+ C below the said stability temperatures.

When the evaporation is carried out in accordance with the details of the present invention, the time necessary for the evaporation at temperatures below the stability temperatures of the solutions is normally somewhat less than that in which the precipitation of solid products is observed.

Since only aqueous formaldehyde solutions are used in the process of the present invention, the minimum temperature for the vaporization is about 25° C.

When the evaporation is carried out in a temperature range below the stability temperatures of the aqueous formaldehyde solutions, the formation of the by-products that contaminate the trioxane is further reduced.

As was mentioned earlier, a fundamental advantage of the process of the present invention consists in the production of a distillate having a composition such that the deposition of polymers of formaldehyde is not caused. For example, when one starts with a reaction mixture containing 60% by weight of formaldehyde, one obtains a distillate with a formaldehydecontent of from 15 to 25% by weight, depending on the conditions used.

On operation in accordance with the details of the present invention and under the conditions described above, the residual aqueous solution that is discharged at the base of the evaporator is richer in formaldehyde than the solution that is fed to the evaporator.

In the practical execution of the process of the present invention, a stage is provided for the polymerization of formaldehyde in which the reaction mixture containing unchanged formaldehyde and trioxane is maintained in equilibrium, or at least under conditions very close to the equilibrium conditions, i.e., in a state in which the concentration of trioxane is a maximum for a given initial formaldehyde concentration.

The reaction mixture is fed continuously to the evaporator, and the residue from the evaporation is recycled to the trimerization reactor after replacement of the quantity of formaldehyde removed in the distillation as unchanged formaldehyde and as trioxane.

Another advantage of the process of the present invention is that the formalin is simultaneously concentrated in the evaporation phase. A consequence of this fact is that the replenishing additions to the trimerization reactor are made with more dilute solutions of formalin.

The trioxane can be recovered from the distillate by extraction with a water-immiscible solvent. Solvents suitable for the purpose are e.g. methylene chloride, chloroform, benzene, toluene, α-chloronaphthalene, or solvents for trioxane that are immiscible with water.

The trioxane is then separated from the organic phase by fractional distillation or crystallization. In the case of separation by distillation it is advantageous to use a solvent having a boiling point that is sufficiently different from that of trioxane.

The formaldehyde collected in the evaporated fraction remains almost completely dissolved in the aqueous phase after extraction of the trioxane, and can thus be recovered and recycled.

It is also possible to subject the products separated at the top of the thin-layer evaporator to distillation. In this way it is possible to separate aqueous solutions having a trioxane content of about 65 to about 70% by weight. The trioxane can be recovered from these last solutions by extraction with organic solvent and distillation of the resulting organic phase.

In every case, by operating in accordance with the procedure of the present invention one obtains trioxane yields of 99% or more based on the formaldehyde introduced, with a purity of 99% or more for the trioxane.

The invention is further illustrated by the following nonlimiting examples.

EXAMPLE 1 (Comparison)

1000 g of 60% aqueous formaldehyde solution and 20 g of sulphuric acid are introduced into a 1.5 liter reactor fitted with an anchor stirrer, a thermometer, and a column with a height of 70 cm and a diameter of 2.5 cm packed with Raschig rings and surmounted by a Toodt head having two condensers.

The mixture is heated to boiling (about 100° C) by means of a thermostatically controlled oil bath. The system operates at atmospheric pressure. Water thermostatically controlled at a temperature of 94° to 95° C is circulated through the first reflux condenser, so that the ascending vapours that have a boiling point above this temperature are condensed and returned to the column. The vapours that pass through are completely condensed in the second condenser at a temperature of 55° C and then collected. By suitable adjustment of the heating in the boiler, 100 g of distillate containing 29.4% by weight of trioxane and 30.6% by weight of formaldehyde, the remainder consisting of water, are collected in one hour.

The reflux ratio has been 2:1. The operation is carried out continuously by feeding a 60% aqueous formaldehyde solution to the boiler in such a way as to keep the quantity and the concentration of formaldehyde in the reaction mixture constant.

During the experiment, progressive deposition of formaldehyde in the form of polymer is observed on the cooler walls at the top of the column, so that after continuous operation for seven hours it was necessary to discontinue the experiment.

The condensate separated at the top of the column, in a quantity of 700 g, is extracted twice in countercurrent, 220 g of methylene chloride being used for each extraction. The organic extract is fractionated by distillation in a packed column. In this way the organic solvent is recovered (distillation temperature 41.5° C), and after a small intermediate fraction consisting of solvent and trioxane, the trioxane fraction is collected (boiling point 114.5° C). The trioxane contains small quantities of formaldehyde. During the distillation of the trioxane, the temperature in the condenser is maintained at 65° C to avoid solidification phenomena.

95% paraformaldehyde is added to the recovered aqueous solution to obtain a 60% aqueous formaldehyde solution. The latter is recycled.

When the operating conditions have been established, 90.7 g of trioxane are obtained per 100 g of formaldehyde introduced.

EXAMPLE 2

1000 g of 60% aqueous formaldehyde solution and 20 g of sulphuric acid are introduced into a 1.5 liter glass flask. The temperature in the reactor is maintained at 100° C by means of a thermostatically controlled oil bath. The reactor is fitted with a thermometer and is maintained at atmospheric pressure.

The solution is removed by means of a syphon pipe and introduced into a laboratory continuous thin-film evaporator maintained at a pressure of 150 mmHg. The fraction evaported at the top is condensed with running water, while the base fraction is returned to the reactor. The pressure difference between the reactor and the evaporator is utilized for he solution feed. The residue time in the evaporator is about 17 seconds, and the evaporation rate is adjusted so that 100 parts of distillate are collected per 1000 parts of solution fed to the evaporator. The temperature at the top of the evaporator is 60° C. .296 g of head fraction containing 20.3% by weight of trioxane and 19.7% by weight of formaldehyde, the remainder consisting of water, are collected in one hour.

The operation is carried out continuously by feeding a 40% aqueous formaldehyde solution to the reactor in such a way as to keep the quantity and concentration (60%) of formaldehyde in the reaction mixture constant.

The system is kept in continuous operation for 12 hours, and no deposition of formaldehyde in the form of polymer is observed in any part of the system.

The total solution colleted at the top in a quantity of 3552 g is extracted twice in countercurrent with methylene chloride, 1090 g of solvent being used for each extraction. The organic extract is then fractionated by distillation in a packed column. In this way methylene chloride is separated first, then a small fraction containing the organic solvent and trioxane, and finally the trioxane distils. The distilled trioxane contains only traces of formaldehyde.

During the distillation of trioxane, the temperature of the condenser is maintained at 65° C to avoid solidification.

The aqueous solution obtained after extraction with organic solvent is adjusted to a formaldehyde concentration of 40% and then recycled to the trioxane synthesis reactor.

When the operating conditions have been established, 99.5 g of trioxane are obtained per 100 g of formaldehyde introduced into the reactor.

EXAMPLE 3 (Comparison)

3000 g of a 60% aqueous formaldehyde solution and 90 g of sulphuric acid are introduced into a 4 liter reactor fitted with an anchor stirrer, a thermometer, and a column with a height of 70 cm and diameter of 2.5 cm packed with Raschig rings and surmounted by a Toodt head with two condensers.

The mixture is heated to boiling (about 100° C) by means of a thermostatically controlled oil bath. The system operates at atmospheric pressure. Water thermostatically controlled at a temperature of 91.5° to 92.5° C is circulated in the first reflux condenser, so that the ascending vapours having a boiling point above this temperature are condensed and returned to the column. The vapours that pass through are completely condensed in the second condenser, which is maintained at 55° C, and are then collected. By suitable adjustment of the heating in the boiler, 153 g of distillate containing 53.5% by weight of trioxane and 19.5% by weight of formaldehyde, the remainder consisting of water, are collected in one hour.

The operation is carried out continuously by addition of a 73% aqueous formaldehyde solution to the boiler in such a way as to keep the quantity and the concentration of formaldehyde in the base solution constant.

The experiment is continued for 8 hours, and the gradual formation of deposits of formaldehyde polymer is observed on the cooler parts of the system.

When steady operating conditions have been established, 28.9 g of trioxane are obtained per 1000 g of 60% formaldehyde solution per hour.

EXAMPLE 4

1000 g of a 60% aqueous formaldehyde solution and 30 g of sulphuric acid are introduced into a 1.5 liter reactor. The temperature of the reactor is maintained at 100° C by means of thermostatically controlled oil. The reactor is fitted with a thermometer and is maintained at atmospheric pressure.

The solution is removed by means of a syphon pipe, and is introduced into a laboratory continuous thin-film evaporator maintained at a pressure of 300 mmHg. The residence time under the evaporation conditions is about 10 seconds. The distillation rate is adjusted in such a way that 80 parts by weight of distillate are collected per 1000 parts by weight of solution fed to the evaporator. The head fraction is condensed, while the base fraction is recycled to the reactor. The temperature at the top of the evaporator is 76° C.

400 g of distillate are collected in one hour, and are then subjected to fractional distillation in a column with a height of 70 cm and a diameter of 2.5 cm containing packing bodies (Raschig rings). Water thermostatically controlled at 65° C is circulated in the condenser. The operation is carried out continuously at atmospheric pressure, and 129 g of distillate containing 65% by weight of trioxane and 4.8% by weight of formaldehyde, the remainder consisting of water, are collected in one hour. The bottom fraction is removed and recycled to the trioxane synthesis reactor.

The solution continuously introduced into the trimerization reactor during operation has a formaldehyde content of 45%. The entire system consisting of the reactor, the evaporator, and the distillation column was kept in operation for 12 hours, and no trouble was encountered.

When steady operating conditions have been established, 83.85 g of trioxane are obtained per 1000 g of 60% aqueous formaldehyde solution present in the reactor per hour.

EXAMPLE 5

1000 g of 78.6% formaldehyde solution and 20 g of sulphuric acid are introduced into a 1.5 liter cylindrical steel reactor. The reactor is fitted with a thermometer and is maintained at a temperature of 110° C by circulation of thermostatically controlled oil in the outer jacket.

The solution is removed by means of a syphon pipe and introduced into a laboratory continuous thin-film evaporator maintained at a pressure of 400 mmHg. The head fraction is collected and condensed, while the bottom fraction is recycled to the reactor. The residence time in the evaporator is 13 seconds. The pressure difference between the reactor and the evaporator is utilized for the solution feed to the evaporator.

The evaporation rate is adjusted so that 125 parts of distillate are obtained per 1000 parts of solution fed to the evaporator. The temperature at the top of the evaporator is 83° C.

Under steady operating conditions, 510 g of head fraction having a trioxane content of 28.4% are collected in one hour.

What we claim is:

1. A process for the separation of trioxane from a solution comprising trioxane, formaldehyde and water, which consists of subjecting the said solution to evaporation in equipment suitable for instantaneous distillation at temperatures, pressures and residence times which substantially eliminate deposition of polymers of formaldehyde on the cooler parts of the apparatus used in said evaporation and minimize the formation of by-products by secondary reactions including the Cannizzaro reaction under the evaporation conditions, with a vaporization and condensing of a quality of from about 5 to about 15% by weight of the solution introduced, and subsequently recovering the trioxane from the trioxane enriched overhead product.

2. Process according to claim 1, wherein the solution containing trioxane and formaldehyde that is subjected to evaporation is obtained by trimerization of formaldehyde in an aqueous solution containing from about 30 to about 85% of weight of formaldehyde, at temperatures of from about 20° to about 150° C in the presence of an acid catalyst.

3. Process according to claim 2, wherein said aqueous solution contains from about 40 to about 80% by weight of formaldehyde and said temperatures are from about 80° to about 110° C.

4. Process according to claim 1, wherein the trioxane is recovered from the evaporated overhead fraction by extraction with a water-immiscible organic solvent followed by separation of the trioxane from the organic solvent by fractional distillation.

5. Process according to claim 1, wherein said equipment operates by the thin-film technique.

6. Process according to claim 1, wherein said equipment operates by the molecular distillation technique.

7. Process according to claim 1, wherein the trioxane is recovered from the evaporated overhead fraction by extraction with a water-immiscible organic solvent solution followed by separation of the trioxane from the organic solvent by crystallization.

8. Process according to claim 1, wherein said evaporation is at a temperature between 20° and 35° C below the stability temperature of said solution.

9. Process according to claim 1, wherein said product contain about 8 to 35% by weight of formaldehyde.

10. Process according to claim 1, wherein the solution comprising trioxane, formaldehyde and water is obtained by trimerization of formaldehyde in a reactor and the about 95 to about 85% by weight of the solution not vaporized is recycled to said reactor.

11. Process according to claim 10, wherein said recycling is accomplished by replacement in said reactor of the quantity of formaldehyde vaporized and removed in the vaporization as unchanged formaldehyde and as trioxane.

12. Process according to claim 1, wherein the trioxane is recovered from the evaporated fraction by distillation of the fraction followed by extraction with an organic solvent and distillation of the resulting organic phase.

13. Process according to claim 1, wherein said evaporation is carried out at pressures of from about 20 to about 700 mm Hg.

14. Process according to claim 13 wherein the evaporation is carried out at pressures of from about 50 to about 500 mm Hg.

15. Process according to claim 1, wherein said evaporation is carried out at temperatures of from about 25° to about 100° C and residence times of from about 3 to about 45 seconds.

* * * * *